Figure 2:
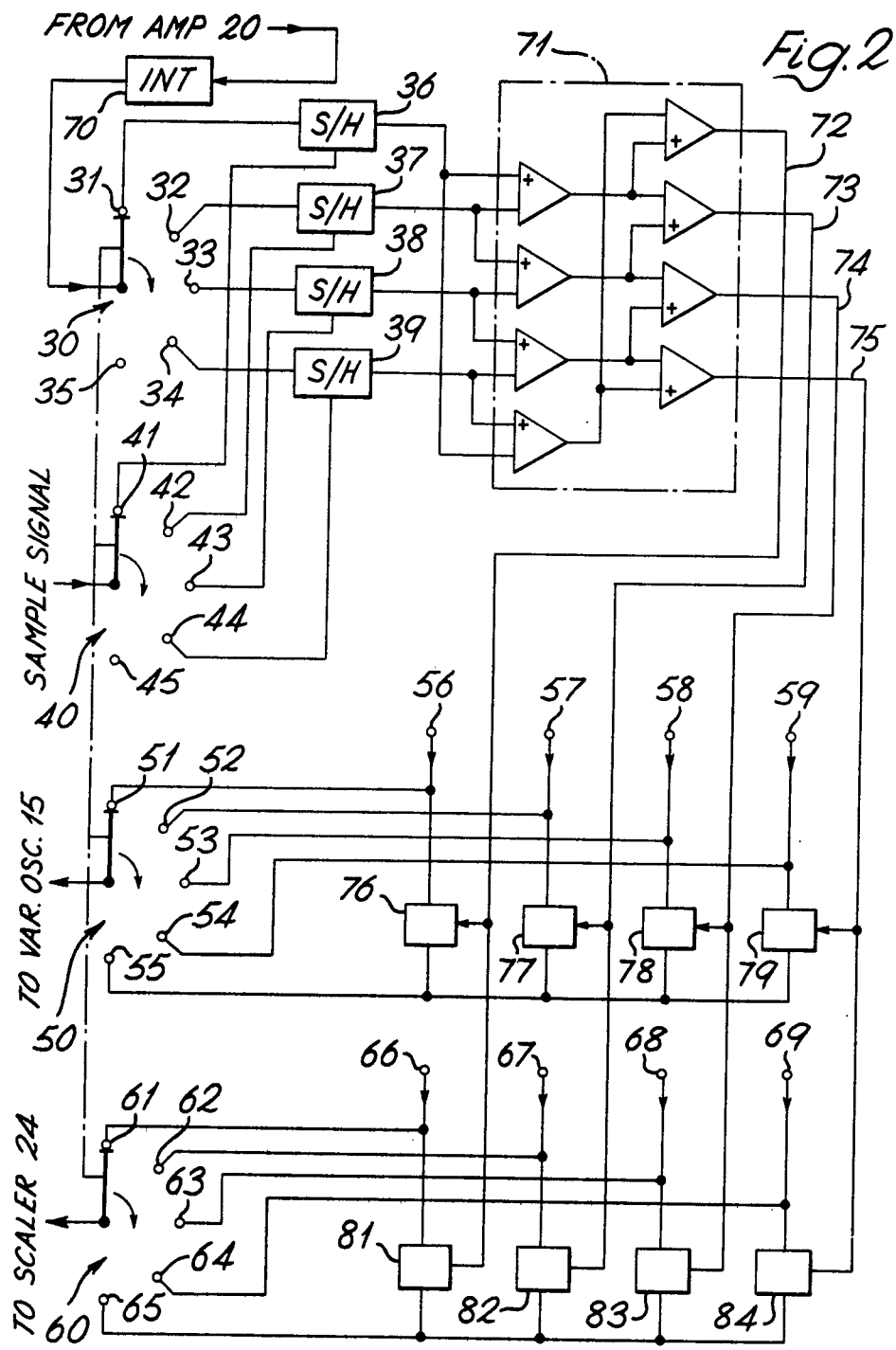

United States Patent [19]

Roberts et al.

[11] 4,434,669
[45] Mar. 6, 1984

[54] APPARATUS FOR TRANSMITTING AND RECEIVING SOUND

[75] Inventors: Victor C. Roberts, London, England; Antonio J. Sainz, Caracas, Venezuela

[73] Assignee: National Research Development Corporation, London, England

[21] Appl. No.: 309,810

[22] Filed: Oct. 8, 1981

[30] Foreign Application Priority Data

Oct. 8, 1980 [GB] United Kingdom ............... 8032438

[51] Int. Cl.³ .............................................. G01F 1/66
[52] U.S. Cl. ................................. 73/861.25; 128/663
[58] Field of Search .................... 73/861.25; 128/663; 367/90, 91

[56] References Cited

FOREIGN PATENT DOCUMENTS 1074070  6/1967  United Kingdom .
1238585  7/1971  United Kingdom .
1332898 10/1973  United Kingdom .
1344778  1/1974  United Kingdom .
1503734  3/1978  United Kingdom .
2022827 12/1979  United Kingdom .
1566916  5/1980  United Kingdom .

OTHER PUBLICATIONS

A. J. Sainz et al., A New Multi-Range Processing System for Directional Ultrasonic Doppler Velocimetry, Mar. 1980, pp. 28-1-28-4.
F. D. McLeod, Directional Doppler Bloodflow Meter, May 1969.

Primary Examiner—Charles A. Ruehl
Attorney, Agent, or Firm—Cushman, Darby & Cushman

[57] ABSTRACT

In an ultrasonic Doppler velocimeter for measuring blood flow it is necessary to change the frequency of insonation according to the site and size of a vessel to be investigated. Several different crystal pairs are employed in a single probe, each pair associated with a different frequency. All of the transmitting crystals are connected in parallel, and all of the receiving crystals are connected in parallel. As a result, the single probe is suitable for investigating blood flow in different blood vessel conditions. Optimum insonation frequency selection is achieved by use of a voltage controlled oscillator, and a frequency control circuit which compares powers received at different frequencies. Signals representative of blood velocities appear at the output of a scaler which ensures that the same velocity provides the same output independently of frequency of insonation.

12 Claims, 3 Drawing Figures

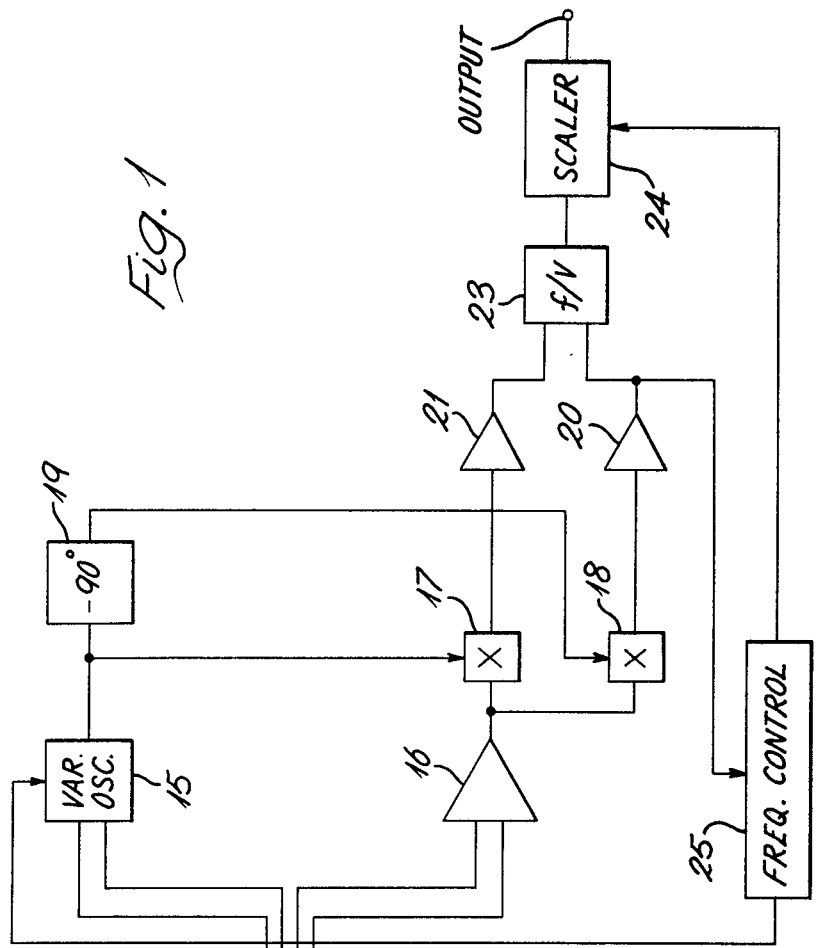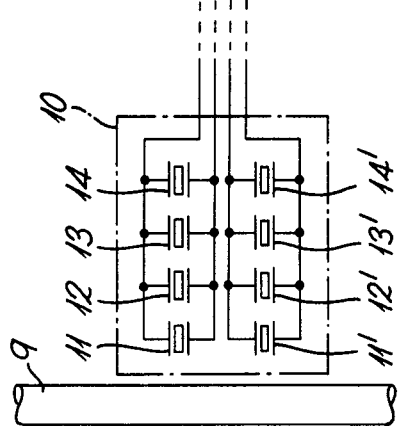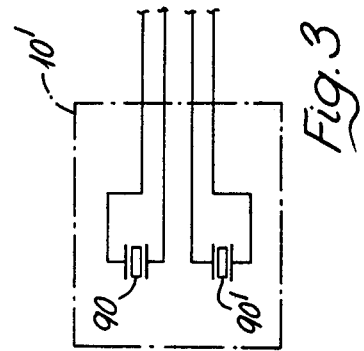

APPARATUS FOR TRANSMITTING AND RECEIVING SOUND

The present invention relates to apparatus for transmitting and receiving ultrasound, particularly, but not exclusively, to Doppler velocimeters for measuring the velocity of blood in blood vessels by making measurements of Doppler frequency change in ultrasound transmitted to and received from a blood vessel liquid whose velocity is to be measured.

In the investigation of occlusive arterial disease, assessment of the degree of circulatory impairment can be made with the aid of an ultrasonic Doppler velocimeter. Such velocimeters are described in: NASA Progress Report NRG 33010074, Cornell University, 1969, "Directional Doppler Flowmeter" McLeod, R. D.; Ultrasound in Medicine and Biology, Volume 2, 1, "Accuracy and Limitations of the Ultrasonic Doppler Blood Velocimeter and Zero Crossing Detector" by Lunt, M. J. (1975); and in the book "Non-Invasive Physiological Measurements" edited by Rolfe, Academic Press, 1979, Chapter 7, "Ultrasonic Doppler Velocimetry" by Roberts and Sainz.

Briefly, in an ultrasound Doppler velocimeter an oscillator is coupled to a transmit crystal in an ultrasonic probe, the probe being positioned so that ultrasound is transmitted as nearly as possible along the axis of a blood vessel in which blood velocity is to be measured. Sound reflected from blood flowing in the vessel is received by a receive crystal in the probe. Due to the Doppler effect a signal having a spectrum of frequencies related to the different velocities of blood flowing in the vessel at different times and in different parts of the cross section of the vessel is generated. Since the frequency of insonation is usually between 2 and 16 mHZ the receive signal is demodulated using the transmit signal and this provides a band of audio signals corresponding to the different velocities. These audio signals can then be converted to voltages proportional to velocity to give a convenient output signal.

In using such apparatus to make measurements of flow of blood or any other fluid, the probe is hand held and typically houses the transmitting and receiving crystals in a coplanar relationship, as described in the publications already mentioned. In order to obtain the signal with the best characteristics at any site of measurement, there is a need to adjust the frequency at which the crystals oscillate. Such optimization frequency can be predicted on theoretical grounds which are described in the publications already mentioned. Typically, apparatus is used at discrete frequencies at either 2, 5 or 10 mHz. Each separate apparatus is equipped with a probe for each frequency and each probe contains a pair of crystals whose frequencies are matched to the desired frequency.

According to the present inventon there is provided apparatus for transmitting and receiving ultrasound, comprising
  an electrical signal source for providing output signals at predetermined selectable frequencies,
  a frequency controller for selecting the frequency provided by the source, and
  probe means coupled to the source for transmitting ultrasound at any said selectable frequency, and for receiving ultrasound at a frequency relatively close to the transmitted frequency.

The main advantage of the present invention is that a single probe may be used for all frequencies required for insonation. This is particularly important in blood flow velocimetry since probe selection does not have to be carried out by the operator.

The predetermined selectable frequencies may either be discrete frequencies such as, for example, 2, 4, 8 and 16 mHz, or continuously variable frequencies over the frequency range.

The probe means may include a plurality of pairs of piezo-electric crystals, one transmitting and one receive crystal in each pair adapted to operate at or relatively close to a predetermined frequency. One surprising advantageous feature of the invention is that the transmit crystals may be connected in parallel with one another and to the signal source; and, similarly, the receive crystals may be connected in parallel with one another and to means for processing signals received to provide an output signal in a required form. Alternatively a single pair of crystals, one for transmission and one for reception, may be provided in which each crystal is adapted to resonate at the predetermined selectable frequencies.

The frequency controller may include means for deriving a signal representative of the power of the signal currently recieved. In an indication of the received power is given, the selectable frequency which provides most power can be determined and manually selected.

Alternatively the frequency controller may include means for selecting each selectable frequency in turn, means for comparing the powers received when the various frequencies are selected and means, coupled to the comparison means, for automatically selecting that frequency which results in most power being received. Automatic frequency selection is clearly an advantageous feature since it means that an operator need not select the required probe or even the required frequency, thus allowing a relatively unskilled operator to use the apparatus.

The processing means may include a single wide band amplifier coupled to the receive crystal or crystals of the probe.

The processing means may also include means for demodulating the output of the amplifier to provide a signal whose frequency and phase is indicative of the velocity and direction of blood flow in a vessel insonated by the probe means. Additionally the processing means may include a frequency-to-voltage converter coupled at the output of the demodulating means, and a scaler controlled by the frequency controller according to the frequency transmitted by the probe to provide an output signal which is substantially independent of the frequency of transmission of ultrasound.

Certain embodiments of the invention will now be described by way of example, with reference to the accompanying drawings, in which:

FIG. 1 is a block schematic diagram of an ultrasonic Doppler velocimeter incorporating the present invention, FIG. 2 is a block diagram of the frequency controller of FIG. 1, and FIG. 3 is a block schematic diagram of an alternative embodiment of the probe of the present invention.

In FIG. 1 a probe 10 contains four ultrasonic transmitting piezo-electric crystals 11 to 14 and four ultrasonic receiving piezo-electric crystals 11' to 14'. The crystals form transmit and receive pairs in which for example the crystals operate at, or in the case of the receive crystals relatively close to (that is allowing for Doppler shift), the following frequencies:

Crystals 11 and 11' - 2 mHz
Crystals 12 and 12' - 4 mHz
Crystals 13 and 13' - 8 mHz
Crystals 14 and 14' - 16 mHz As has been mentioned above, different frequencies of insonation are optimum under different conditions such as the position in the body and the cross-sectional area of a blood vessel 9. The apparatus of the drawing automatically selects a frequency at which a particular crystal pair is resonant as described below. The number of crystal pairs is not limited to four but in practice it is thought that the number of such pairs for practical uses may vary between two and six.

The transmit crystals 11, 12, 13 and 14 receive excitation signals from a variable frequency oscillator 15 so that if one particular frequency is to be selected the variable oscillator passes a signal at this frequency to the probe and the crystal which is resonant at this frequency transmits ultrasound. The oscillator 15 may itself be crystal controlled and in the well known form in which a trimmer capacitor is connected in parallel with a crystal. The basis of this oscillator was described in U.K. Pat. No. 537167 and it is further discussed in the paper entitled "Technical Topics" by Pat Hawker G3VA in Radio Communication for December 1973 at page 853. Since, as is described below, the frequency generated by the oscillator 15 is voltage controlled, the above mentioned trimmer capacitor is replaced by a capacitor whose capacitance varies in accordance with an applied control voltage (such capacitors are known as Varicaps). In the present embodiment four different voltage sources are available for application to the Varicap, one source corresponding to each transmit crystal.

Ultrasound signals reflected from blood flowing in insonated vessel 9 are received by the four receive crystals 11' to 14' which are connected in parallel to the input of a wide band amplifier 16 which covers the band of the four frequencies available from the oscillator 15. Alternatively a tuned amplifier may be used which has tuning components automatically selected when the frequency of the oscillator 15 is selected.

Signals at the output of the amplifier 16 are demodulated by means of multipliers 17 and 18 which receive reference signals from the oscillator 15 at the frequency currently applied to the crystals 11 to 14 in the probe. The reference signal for the multiplier 18 is phase retarded by 90° in a circuit 19. The signals from the multipliers 18 and 19 are applied to amplifiers 20 and 21 whose outputs indicate by the audio frequency produced, the velocity of blood in the vessel insonated; and by relative phase, the direction of blood flow. The object of using the two multipliers 17 and 18 to demodulate the signal from the probe is to give an output which is dependent for its sign on the direction of blood flow.

A frequency to voltage converter 23 which includes a phase sensor provides an output signal whose voltage magnitude and sign are determined by blood flow velocity and direction, respectively. After the optimum frequency of transmission has been selected, it is still found that the amplitude of the received signal is proportional to the frequency of insonation and for this reason the output signal of the frequency to voltage converter 23 is applied to a scaler 24 which may be in the form of a variable gain amplifier, with gain controlled according to the frequency of insonation. The gain of this amplifier is inversely proportional to the insonation frequency.

In order to provide the control functions mentioned below, the audio signal to the output of the amplifier 20 is applied to a frequency control circuit 25 which has the function of selecting the correct output frequency for the oscillator 15 and selecting the correct gain for the scaler 24. The controller 25 comprises a sweep circuit for sweeping the oscillator 15 through the available transmit frequencies, a circuit for measuring the audio power received at the output of the amplifier 20, and a logic circuit for selecting the frequency at which the highest power is received.

Frequency sweeping can be carried out on operation of a manual control, or automatically either after equal time intervals or in synchronism with one or a group of cardiac cycles. A trigger signal is developed which stems either from the operation of the manual control or from time elapsed or from the detection of some point in the cardiac cycle or in a group of such cycles. This trigger signal causes a counter to step through its various states and in each state one of the four possible voltages is applied to the Varicap in the oscillator 15 so that one of the four possible frequencies is generated.

A circuit which may be used as the controller 25 is shown in FIG. 2 where the output from the amplifier 20 is applied to a moving arm of a switch 30 by way of an integrator 70. The switch 30 has five contacts 31 to 35 any one of which can be selected by the arm. The contacts 31 to 34 are connected to sample and hold circuits 36 to 39, respectively, which receive a sample signal by way of contacts 41 to 44 of a switch 40.

Four reference voltages capable of selecting the four frequencies 2, 4, 8 and 16 mHz when passed to oscillator 15 are applied to terminals 56 to 59 and thence to terminals 51 to 54, respectively, of a switch 50, and similarly four further reference voltages are applied to terminals 61 to 64 of the switch 60 by way of terminals 66 to 69, respectively.

The switches 30 to 60 are ganged together and when in manual form, if the optimum insonation frequency is to be selected, the arms of the switches are rotated clockwise from the contact having the lowest designation to the contact having the highest designation. Thus in the first switch position the reference voltage for the 2 mHz signal leaves the switch 50 causing the oscillator 15 to generate a 2 mHz signal for application to the probe. As a result an output signal is received by the integrator 70 and after integration is applied to the sample and hold circuit 36. As the arms of the switches are rotated through the first four positions the output signals of the sample and hold circuits 36 to 39 represent the powers of ultrasound received from the probe at the various frequencies. By means of a group of interconnected level comparators shown within the chain dotted line 71 an output signal is produced on that one of four output lines 72 to 75 which corresponds to the frequency at which the highest level of received ultrasound occurs. The lines 72 to 75 are used to control gates 76 to 79 so that the reference voltage which selects the frequency which produces the most ultrasound is applied to the terminal 55 of the switch 50. Thus when the arm of the switch 50 reaches the contact 55 the reference selected voltage is applied to the oscillator 15.

By a similar arrangement of gates 81 to 84 the selected reference voltage appears at the output of the switch 60 for application to the scaler 24. Within the scaler a circuit reponsive to the reference voltages selects the required gain to ensure that all outputs from the scaler for similar velocities are equal.

As described, an operator can select the optimum frequency at any time by rotating the ganged switches 30 to 60 but if the switches are implemented digitally then it is arranged that the dwell position 35, 45, 55 and 65 is held for a time which very much exceeds the times held by the other switch positions. When implemented digitally sweep by the switches may, for example, be initiated by a pulse obtained from an electrocardiogram and the sweep through the first four positions may be executed in the first few milliseconds of the cardiac beat.

In practice of course the switches 30 to 60 are usually in solid state form.

In the frequency-to-voltage converter 23, audio signals from the amplifier 20 are applied to a frequency shifting circuit which employs a carrier frequency of, for example, 80 kHz. The object of carrying out this frequency shift is to allow a relatively short time constant to be used for smoothing. Full wave rectification at audio would require a very long time constant much longer than the time required for a suitable sweep through the frequencies which should be of the order of one millisecond. A suitable frequency shifter is described under the title "The Generation of SSB (Single Side Band) Signals" in Chapter 7—Modulation, Section 7-10 of the book "Analysis, Transmission and Filtering of Signals", by Javid and Brenner, published in 1973 by McGraw Hill. Briefly the frequency shifting circuit comprises two multipliers which receive the audio signal, and the audio signal phase retarded by 90°, respectively. The two multipliers each receive an 80 kHz reference signal and the multiplier which receives the undelayed audio signal receives the 80 kHz signal phase retarded by 90°. The outputs of the two multipliers are applied to the inputs of a differential amplifier and the frequency shifted output is obtained at the output of the amplifier.

A suitable frequency-to-voltage current is the phase-locked loop circuit described in "Blood flow velocity and acceleration measurement by Doppler shift ultrasound", Sainz, A. J., Roberts, V. C., Pinardi, G., Lindenauer, S. M., in Non-Invasive Clinical Measurement, edit. Taylor D., Whamond, J., Pitman Medical, Tunbridge Wells.

The signal from the frequency shifting circuit is full wave rectified and smoothed, using a time constant which provides smoothing over, for example, about 5 cycles of the 80 kHz signal.

A logic circuit in the frequency controller 25 samples the smoothed rectified output at four different times during the frequency sweep corresponding to the reception of signals at the four different frequencies. The sampled signals are applied to sample and hold circuits whose outputs are coupled to comparators to allow the highest sampled output to be identified. The logic circuit then causes the oscillator 15 to switch back to that voltage which when applied to the Varicap selects the output frequency which produced the highest output power at output of amplifier 20. At the same time a corresponding signal is applied to control the gain of scaler 24.

In another embodiment of the invention illustrated in FIG. 3, the crystals 11 to 14 may be replaced by a single wide band crystal 90 in probe 10', which for example is adapted to oscillate at four frequencies. Similarly, the crystals 11' to 14' are replaced by a single crystal 90' formed in the same way. Techniques of crystal cutting and choice of lattice size, which allow a single crystal to be resonant at a number of different frequencies, are known to crystal manufacturers.

In a development of this modification the single crystal pair which replaces the four pairs of crystals shown in the drawing is resonant at a large number of discrete frequencies so that it can be regarded as being variable over the whole frequency band from, for example, 2 mHz to 16 mHz. Additionally a Varicap trimmer may be connected across the crystal to allow frequencies between the discrete frequencies to be used. When such a crystal is used the voltage applied to the Varicap in the oscillator 15 is also continuously variable and in selecting the optimum frequency a peak in the output from the frequency shifter is detected by the logic circuit and the time of occurrence of this peak in relation to the frequency sweep is determined to select the optimum frequency.

It will be clear from the embodiment of the invention specifically described that the invention can be put into practice in many other ways. For example other forms of demodulation of the signal from the probe may be used and in particular an "intermediate frequency" may be employed. The frequency controller and the variable frequency oscillator may also be implemented in other ways.

The invention can be applied in many fields, particularly where the velocity of a fluid is to be measured, or a signal which depends on fluid velocity is to be derived.

We claim:
1. Apparatus for transmitting and receiving ultrasound, comprising:
   electrical signal generating means for providing output signals at predetermined selectable frequencies;
   probe means coupled to the generating means for transmitting ultrasound at any said selectable frequency, and for receiving ultrasound signals at a frequency relatively close to the transmitted frequency; and
   frequency controlling means for automatically selecting at least one of said output signals including:
      means for comparing the powers of doppler-shifted ultrasound signals received by said probe means at said predetermined frequencies, and
      means for selecting the one of said output signals which results in most doppler-shifted ultrasound signal power being received.
2. Apparatus according to claim 1 wherein said frequency controlling means further includes means for instructing said generating means to generate each selectable frequency in turn, said comparing means comparing the powers received when said instructing means causes the various frequencies to be generated.
3. Apparatus according to claim 1 further comprising processing means for demodulating the ultrasound signals received by said probe means to provide a signal whose frequency and phase are indicative of the velocity and direction of blood flow in a vessel insonated by said probe means.
4. Apparatus according to claim 3 further comprising a frequency-to-voltage converter coupled at the output of said demodulating means, and a scaler controlled by said frequency controlling means according to the frequency transmitted by said probe means to provide an output signal which is substantially independent of the frequency of transmission of ultrasound.

5. Apparatus according to claim 1 wherein said selectable frequencies are discrete frequencies.

6. Apparatus according to claim 5 wherein said probe means includes a plurality of pairs of piezo-electric elements, with one transmit element and one receive element in each pair adapted to operate at, or relatively close to, a predetermined one of said selectable frequencies.

7. Apparatus according to claim 6 wherein said transmit elements are connected in parallel with one another and to said generating means.

8. Apparatus according to claim 6 further comprising means for processing the ultrasound signals received by the probe means to provide an output signal in a required form, said receive elements being connected in parallel with one another and to said processing means.

9. Apparatus according to claim 1 wherein said probe means includes a single pair of piezo-electric elements with one for transmission and one for reception, each of said elements being adapted to resonate at all said predetermined selectable frequencies.

10. Apparatus according to claim 1 wherein said probe means includes at least one piezo-electric element for transmitting ultrasound and a plurality of second piezo-electric elements for receiving ultrasound.

11. Apparatus according to claim 1 wherein said proble means includes at least one piezo-electric element for receiving ultrasound and a plurality of second piezo-electric elements for transmitting ultrasound.

12. Apparatus according to claim 1 wherein:
said comparing means further comprises means for determining and indicating the value of the ultrasound signal power received by said probe means; and
the selecting means of the frequency controlling means includes a manual control for selecting the output signal of the signal generating means.

* * * * *